(12) United States Patent
Koizumi et al.

(10) Patent No.: US 6,830,908 B2
(45) Date of Patent: Dec. 14, 2004

(54) GLYCOSYLTRANSFERASE AND DNA ENCODING THE SAME

(75) Inventors: Satoshi Koizumi, Tokyo (JP); Tetsuo Endo, Tokyo (JP); Kazuhiko Tabata, Yamaguchi (JP); Akio Ozaki, Tokyo (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 10/218,381

(22) Filed: Aug. 15, 2002

(65) Prior Publication Data

US 2003/0013175 A1 Jan. 16, 2003

Related U.S. Application Data (62) Division of application No. 09/601,519, filed as application No. PCT/JP99/00321 on Jan. 21, 1999, now Pat. No. 6,475,761.

(30) Foreign Application Priority Data

Feb. 4, 1998 (JP) .............................................. 11-23389

(51) Int. Cl.[7] .......................... C12N 9/10; C12N 1/20; C12N 15/00; C07H 21/04; C12P 19/00

(52) U.S. Cl. ................. 435/193; 435/252.3; 435/320.1; 435/252.33; 435/72; 435/74; 435/822; 435/84; 536/23.2; 536/23.7

(58) Field of Search .............................. 435/193, 252.3, 435/252.33, 320.1, 72, 74, 84, 822; 536/23.2, 23.7

(56) References Cited

U.S. PATENT DOCUMENTS 6,475,761 B1 * 11/2002 Koizumi et al. ............ 435/193

FOREIGN PATENT DOCUMENTS

| JP | 2-27987 | 1/1990 |
|---|---|---|
| WO | 96/10086 | 4/1996 |
| WO | 96/40893 | 12/1996 |
| WO | 01/00796 | 1/2001 |

OTHER PUBLICATIONS

Shapers, et al., "Characterization of the Full Length cDNA for Murine . . . ", The Journal of Biological Chemistry, vol. 263, No. 21 (1988), pp. 10420–10428.

Masri, et al., "Identification of the Full–Length Coding Sequence for Human . . . ", Biochmical and Biophysical Research Communications, vol. 157, No. 2 (1988), pp. 657–663.

D'Agostaro, et al., "Cloning of cDNA encoding the membrane–bound for of . . . ", Eur. J. Biochem., vol. 183 (1989), pp. 211–217.

Kolkman, et al., "Capsular Polysaccharide synthesis in . . . ", Molecular Microbiology, vol. 26 (1997), pp. 197–208.

Chan, et al., "The biosynthesis of Lewis X in *Helicobacter pylori*", Glycobiology, vol. 5, No. 7 (1995), pp. 683–688.

Tomb, et al., "The complete genome sequence of the gastric . . . ", Nature, vol. 388 (1997), pp. 539–547.

Boeggeman, et al., "Expression of deletion constructs of bovine . . . ", Protein Engineering, vol. 6, No. 7 (1993), pp. 779–785.

(List continued on next page.)

*Primary Examiner*—Tekchand Saidha
(74) *Attorney, Agent, or Firm*—Fitzpatrick, Cella, Harper & Scinto (57) ABSTRACT

The present invention provides a protein having β1,4-galactosyltransferase activity, DNA encoding the protein, a recombinant DNA comprising the DNA, a transformant carrying the recombinant DNA, a process for producing β1,4-galactosyltransferase by using the transformant, and a process for producing a galactose-containing carbohydrate by using the transformant.

6 Claims, 3 Drawing Sheets

OTHER PUBLICATIONS

Sequence Search Alignments Only—WO9640893–A1.

Karlin, et al. "Applications and statistics for multiple high–scoring segments in molecular sequences", *Proc. Natl. Acad. Sci.*, vol. 90 (1993), pp. 5873–5877.

Alm, et al., "Genomic–sequence comparison of two unrelated isolates of the human gastric pathogen *Helicobactor pylori*", *Nature*, vol. 397 (1999), pp. 176–180.

Correction to Alm, et al. "Genomic–sequence comparison of two unrelated isolates of th human gastric pathogen *Helicobactor pylori*", *Nature*, vol. 397 (1999), p. 719.

* cited by examiner

SEQUENCE LISTING

<160> NUMBER OF SEQ ID NOS: 6

<210> SEQ ID NO 1
<211> LENGTH: 273
<212> TYPE: PRT
<213> ORGANISM: Helicobacter pylori

<400> SEQUENCE: 1

```
Leu Arg Val Phe Ile Ile Ser Leu Asn Gln Lys Val Cys Asp Thr Phe
 1               5                  10                  15

Gly Leu Val Phe Arg Asp Thr Thr Leu Leu Asn Asn Ile Asn Ala
                20                  25                  30

Thr His His Gln Ala Gln Ile Phe Asp Ala Ile Tyr Ser Lys Thr Phe
            35                  40                  45

Glu Gly Gly Leu His Pro Leu Val Lys Lys His Leu His Pro Tyr Phe
     50                  55                  60

Ile Thr Gln Asn Ile Lys Asp Met Gly Ile Thr Thr Asn Leu Ile Ser
 65                  70                  75                  80

Glu Val Ser Lys Phe Tyr Tyr Ala Leu Lys Tyr His Ala Lys Phe Met
                 85                  90                  95

Ser Leu Gly Glu Leu Gly Cys Tyr Ala Ser His Tyr Ser Leu Trp Glu
            100                 105                 110

Lys Cys Ile Glu Leu Asn Glu Ala Ile Cys Ile Leu Glu Asp Asp Ile
        115                 120                 125

Thr Leu Lys Glu Asp Phe Lys Glu Gly Leu Asp Phe Leu Glu Lys His
    130                 135                 140

Ile Gln Glu Leu Gly Tyr Val Arg Leu Met His Leu Leu Tyr Asp Pro
145                 150                 155                 160

Asn Val Lys Ser Glu Pro Leu Asn His Lys Asn His Glu Ile Gln Glu
                165                 170                 175

Arg Val Gly Ile Ile Lys Ala Tyr Ser His Gly Val Gly Thr Gln Gly
            180                 185                 190

Tyr Val Ile Thr Pro Lys Ile Ala Lys Val Phe Lys Lys His Ser Arg
        195                 200                 205

Lys Trp Val Val Pro Val Asp Thr Ile Met Asp Ala Thr Phe Ile His
    210                 215                 220

Gly Val Lys Asn Leu Val Leu Gln Pro Phe Val Ile Ala Asp Asp Glu
225                 230                 235                 240

Gln Ile Ser Thr Ile Ala Arg Lys Glu Glu Pro Tyr Ser Pro Lys Ile
                245                 250                 255

Ala Leu Met Arg Glu Leu His Phe Lys Tyr Leu Lys Tyr Trp Gln Phe
            260                 265                 270

Val
```

<210> SEQ ID NO 2
<211> LENGTH: 819
<212> TYPE: DNA
<213> ORGANISM: Helicobacter pylori

<400> SEQUENCE: 2

```
ttgcgtgttt ttatcatttc tttaaatcaa aaagtgtgcg atacatttgg tttggttttt    60
agagacacca cgactttact caataatatt aatgccaccc accaccaagc gcaaattttt   120
gatgcgattt attctaaaac ttttgaaggc gggttgcacc ccttagtgaa aaagcattta   180
```

```
caccottatt tcatcacgca aaacatcaaa gacatgggga ttacaaccaa tctcatcagt    240
gaggtttcta agttttatta cgctttaaaa taccatgcga agtttatgag cttgggggag    300
cttgggtgct atgcgagcca ttattccttg tgggaaaaat gcatagaact caatgaagcg    360
atctgtattt tagaagacga tataaccttg aaagaggatt ttaaagaggg attggatttt    420
ttagaaaaac acatccaaga gttaggctat gttcgcttga tgcatttatt atatgacccc    480
aatgttaaaa gtgagccatt gaaccataaa accacgaga tacaagagcg tgtggggatc     540
attaaagctt atagtcatgg ggtggggacg caaggctatg tgatcacgcc caagattgcc    600
aaagttttta aaaacacag ccgaaaatgg gttgttcctg tggatacgat aatggacgct     660 actttatcc atggcgtgaa aaatctggtg ttacaaccttt ttgtgatcgc tgatgatgag    720
cagatctcta cgatagcacg aaaagaagaa cctatagcc ctaaaatcgc cttaatgaga     780
gaactccatt ttaaatattt gaaatattgg cagtttgta                          819
```

```
<210> SEQ ID NO 3
<211> LENGTH: 24
<212> TYPE: DNA
<213> ORGANISM: Artificial Sequence
<220> FEATURE:
<223> OTHER INFORMATION: Synthetic DNA

<400> SEQUENCE: 3
cctatgagct cttttatcat ttct                                           24

<210> SEQ ID NO 4
<211> LENGTH: 23
<212> TYPE: DNA
<213> ORGANISM: Artificial Sequence
<220> FEATURE:
<223> OTHER INFORMATION: Synthetic DNA

<400> SEQUENCE: 4
agcggatcct aaaaagtctt agt                                            23

<210> SEQ ID NO 5
<211> LENGTH: 30
<212> TYPE: DNA
<213> ORGANISM: Artificial Sequence
<220> FEATURE:
<223> OTHER INFORMATION: Synthetic DNA

<400> SEQUENCE: 5
ggtaaagctt atgcagcctc tggtttccgt                                     30

<210> SEQ ID NO 6
<211> LENGTH: 29
<212> TYPE: DNA
<213> ORGANISM: Artificial Sequence
<220> FEATURE:
<223> OTHER INFORMATION: Synthetic DNA

<400> SEQUENCE: 6
aaacggatcc ttggctctgc attagatct                                      29
```

GLYCOSYLTRANSFERASE AND DNA ENCODING THE SAME

CROSS-REFERENCE TO THE RELATED APPLICATION

This application is a division of application Ser. No. 09/601,519 filed on Aug. 2, 2000, now U.S. Pat. No. 6,475,761, which is a 371 of PCT/JP99/00321, filed Jan. 21, 1999.

TECHNICAL FIELD

The present invention relates to a protein having β1,4-galactosyltransferase activity, DNA encoding the protein, a recombinant DNA comprising the DNA, a transformant carrying the recombinant DNA, a process for producing β1,4-galactosyltransferase by using the transformant, and a process for producing a galactose-containing carbohydrate by using the transformant.

BACKGROUND ART

The β1,4-galactosyltransferase genes so far obtained are those derived from animals [J. Biol. Chem., 263, 10420 (1988); Biochem. Biophys. Res. Commun., 157, 657 (1988); Eur. J. Biochem., 183, 211 (1989)], those derived from *Neisseria gonorrhoeae* (WO 96/10086) and those derived from *Streptococcus pneumoniae* [Mol. Microbiol., 26, 197 (1997)].

O-antigens of lipopolysaccharides of *Helicobacter pylori* have the same structures as the Lewis X [Gal β1–4 (Fucα1–3)GlcNAc] and Lewis Y [Fucα1–2Gal β1–4 (Fucα1–3)GlcNAc] epitopes of mammals, and *Helicobacter pylori* is expected to possess β1,4-galactosyltransferase activity [Glycobiology, 5, 683 (1995)]. In *Helicobacter pylori*, however, a protein highly homologous to known β1,4-galactosyltransferases has not been found and a β1,4-galactosyltransferase gene has not been specified [Nature, 388, 539 (1997)].

DISCLOSURE OF THE INVENTION

An object of the present invention is to provide a protein having β1,4-galactosyltransferase activity, DNA encoding the protein, a process for producing a protein having β1,4-galactosyltransferase activity by using the DNA, and a process for producing a galactose-containing carbohydrate by using the above protein.

The present inventors made an intensive investigation to attain the object. As a result, a β1,4-galactosyltransferase gene so far unspecified has been obtained by screening of *Helicobacter pylori* genomic DNA library for the gene encoding a protein having β1,4-galactosyltransferase activity and its sequence has been determined. The present invention has been completed on the basis of this result.

Thus, the first aspect of the present invention provides a protein which is selected from the group consisting of:
  (a) a protein having the amino acid sequence shown in SEQ ID NO: 1; and
  (b) a protein having β1,4-galactosyltransferase activity and having an amino acid sequence wherein one to several amino acid residues are deleted, substituted or added in the amino acid sequence of the protein of (a).

The above deletion, substitution or addition of amino acid residues can be caused by site-directed mutagenesis, which is a technique known in the art at the time of filing of the present application. The expression "one to several amino acid residues" is intended to mean amino acid residues in such numbers that can be deleted, substituted or added by site-directed mutagenesis.

Such a protein having β1,4-galactosyltransferase activity and having an amino acid sequence wherein one to several amino acid residues are deleted, substituted or added can be produced according to the methods described in Molecular Cloning, A Laboratory Manual, Second Edition, Cold Spring Harbor Laboratory Press (1989) (hereinafter referred to as Molecular Cloning, Second Edition); Current Protocols in Molecular Biology, John Wiley & Sons (1987–1997) (hereinafter referred to as Current Protocols in Molecular Biology); Nucleic Acids Research, 10, 6487 (1982); Proc. Natl. Acad. Sci. USA, 79, 6409 (1982); Gene, 34, 315 (1985); Nucleic Acids Research, 13, 4431 (1985); Proc. Natl. Acad. Sci. USA, 82, 488 (1985), etc.

The second aspect of the present invention provides DNA encoding the above protein, DNA having the nucleotide sequence shown in SEQ ID NO: 2, and DNA which hybridizes to the DNA having the nucleotide sequence shown in SEQ ID NO: 2 under stringent conditions and which encodes a protein having β1,4-galactosyltransferase activity.

The "DNA which hybridizes under stringent conditions" refers to DNA which is obtained by colony hybridization, plaque hybridization or Southern hybridization using the DNA having the nucleotide sequence shown in SEQ ID NO: 2 as a probe. Such DNA can be identified, for example, by performing hybridization at 65° C. in the presence of 0.7–1.0 M sodium chloride using a filter with colony- or plaque-derived DNA immobilized thereon and then washing the filter at 65° C. using 0.1 to 2-fold concentrated SSC solution (SSC solution: 150 mM sodium chloride and 15 mM sodium citrate).

Hybridization can be carried out according to the methods described in laboratory manuals such as Molecular Cloning, Second Edition; Current Protocols in Molecular Biology; and DNA Cloning 1: Core Techniques, A Practical Approach, Second Edition, Oxford University (1995). The hybridizable DNA is, for example, DNA having at least 80% homology, preferably 95% or more homology to the nucleotide sequence shown in SEQ ID NO: 2.

The third aspect of the present invention provides a recombinant DNA which is obtained by inserting the above DNA into a vector.

The fourth aspect of the present invention provides a transformant which is obtained by introducing the above recombinant DNA into a host cell.

The fifth aspect of the present invention provides a process for producing the above protein which comprises culturing the above transformant in a medium, allowing the protein to form and accumulate in the culture, and recovering the protein from the culture.

The sixth aspect of the present invention provides a process for producing a galactose-containing carbohydrate which comprises allowing a culture of the above transformant or a treated matter thereof as an enzyme source, an acceptor carbohydrate and uridine diphosphogalactose to be present in an aqueous medium, transferring galactose to the acceptor carbohydrate by β1,4 linkage to form and accumulate the galactose-containing carbohydrate in the aqueous medium, and recovering the galactose-containing carbohydrate from the aqueous medium.

The present invention is described in detail below.
  1. Preparation of the DNA of the Present Invention
  (1) Construction of a Genomic DNA Library
    The DNA of the present invention can be prepared from a microorganism belonging to the genus Helicobacter.

Examples of suitable microorganisms belonging to the genus Helicobacter are strains of *Helicobacter pylori*, specifically, *Helicobacter pylori* NCTC 11637.

A microorganism belonging to the genus Helicobacter is cultured by a known method [e.g., Mol. Microbiol., 20, 833 (1996)].

After the culturing, the chromosomal DNA of the microorganism is isolated and purified by a known method (e.g., Current Protocols in Molecular Biology).

The obtained chromosomal DNA is cleaved with an appropriate restriction enzyme and fractionated by means such as sucrose density gradient ultracentrifugation, and DNA fragments of 2–6 kb are recovered.

According to a conventional method (e.g., Molecular Cloning, Second Edition), the recovered DNA fragment is inserted into an expression vector for *Escherichia coli* at a site downstream of the promoter and the thus constructed recombinant DNA is introduced into *Escherichia coli* to prepare a genomic DNA library.

Suitable expression vectors include pBTrp2, pBTac1 and pBTac2 (all available from Boehringer Mannheim), pKK233-2 (Pharmacia), pSE280 (Invitrogen), pGEMEX-1 (Promega), pQE-8 (QIAGEN), pKYP10 (Japanese Published Unexamined Patent Application No. 110600/83), pKYP200 [Agric. Biol. Chem., 48, 669 (1984)], pLSA1 [Agric. Biol. Chem., 53, 277 (1989)], pGEL1 [Proc. Natl. Acad. Sci. USA, 82, 4306 (1985)], pBluescript II SK+ (Stratagene), pBluescript II SK (−) (Stratagene), pTrs30 (FERM BP-5407, pTrs32 (FERM BP-5408), pGHA2 (FERM BP-400), pGKA2 (FERM BP-6798), pTerm2 (Japanese Published Unexamined Patent Application No. 22979/91, US 4686191, US 4939094 and US 5160735), pEG400 [J. Bacteriol., 172, 2392 (1990], pGEX (Pharmacia), pET-3 (Novagen), pSupex, pUB110, pTP5, pC194, pTrxFus (Invitrogen), pMAL-c2 (New England Biolabs), pUC19 [Gene, 33, 103 (1985)], pSTV28 (Takara Shuzo Co., Ltd.), pUC118 (Takara Shuzo Co., Ltd.), pPA1 (Japanese Published Unexamined Patent Application No. 233798/88), etc.

Examples of *Escherichia coli* strains are *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Escherichia coli* MP347 and *Escherichia coli* NM522.

Introduction of the recombinant DNA can be carried out by any of the methods for introducing DNA into the above host cells, for example, the method using calcium ion [Proc. Natl. Acad. Sci, USA, 69, 2110 (1972)], the protoplast method (Japanese Published Unexamined Patent Application No. 248394/88) and electroporation [Nucleic Acids Research, 16, 6127 (1998)].

(2) Screening and Preparation of the DNA of the Present Invention

The *Escherichia coli* cells prepared above as a genomic DNA library are cultured by a conventional method, for example, in LB medium [10 g/l Bacto-tryptone (Difco Laboratories Inc.), 5 g/l yeast extract (Difco Laboratories Inc.), and 5 g/l NaCl (pH 7.2)] at 20–45° C. for 5–24 hours.

After the culturing, the obtained culture is centrifuged to obtain wet cells.

The wet cells are used for screening for an *Escherichia coli* strain having a β 1,4-galactosyltransferase gene by detecting β 1,4-galactosyltransferase activity. Screening can be carried out according to a know method [J. Biol. Chem., 271, 28271 (1996)] or in the following manner. The wet cells can be stored at −20° C. and can be used after thawing, according to need.

Reaction is carried out at 37° C. for 16 hours using 0.02 ml of a reaction mixture comprising the above wet cells, 50 mM MES [2-(N-morpholino)ethanesulfonic acid, monohydrate] (pH 6.0), 10 mM $MnCl_2$, 0.2 mM uridine diphosphogalactose (UDP-Gal), 0.4% Nymeen S-215 and 0.2 mM fluorescence-labeled LNT-2 (GlcNAc β1–3Galβ1–4Glc) prepared by the method described later in Reference Example 1.

After the completion of reaction, the reaction mixture is centrifuged to remove the cells and to obtain the supernatant.

The supernatant is put on a silica gel-60 TLC plate (Merck & Co.), followed by development with ethyl acetate:methanol:water:acetic acid =7:2:1:0.1. After the development, the plate is dried and detection of spots is made with UV 365 nm.

The same procedure as above is repeated using β1,4-galactosyltransferase (Sigma Chemical Co.) in place of the *Escherichia coli* wet cells and the spot on TLC which corresponds to fluorescence-labeled lacto-N-neotetraose (LNnT: Galβ1–4GlcNAcβ1–3Galβ-1,4Glc) (fluorescence-labeled LNnt) formed by this procedure is confirmed.

An *Escherichia coli* strain giving a spot at the same position on the TLC plate as fluorescence-labeled LNnT in the above procedure using wet cells is selected as a strain carrying a β1,4-galactosyltransferase gene.

The desired DNA can be obtained from the selected clone according to a conventional method (e.g., Molecular Cloning, Second Edition).

The obtained DNA, as such or after cleavage with appropriate restriction enzymes, is inserted into a vector by a conventional method, and then analyzed by a DNA sequencing method usually employed, e.g., the dideoxy method [Proc. Natl. Acad. Sci. USA, 74, 5463 (1977)] or by the use of a DNA sequencer, e.g., 373A DNA Sequencer (Perkin-Elmer Corp.) to determine its nucleotide sequence.

Suitable vectors for the insertion of the above DNA include pBluescript KS(+) (Stratagene), pDIRECT [Nucleic Acids Research, 18, 6069 (1990)], pCR-Script Amp SK(+) (Stratagene), pT7Blue (Novagen), pCR II (Invitrogen), pCR-TRAP (GenHunter), $pNoTA_{T7}$ (5Prime→3Prime), etc.

An example of the DNA having a novel nucleotide sequence which is obtained by the above method is the DNA having the sequence shown in SEQ ID NO: 2.

One example of an *Escherichia coli* strain carrying the DNA having the sequence shown in SEQ ID NO: 2 is *Escherichia coli* NM522/pPT1 (FERM BP-6226).

The desired DNA can be obtained by PCR [PCR Protocols, Academic Press (1990)] using primers prepared based on the nucleotide sequence determined as above and, as a template, a genomic DNA library.

The desired DNA can also be prepared by chemical synthesis based on the determined nucleotide sequence of the DNA using a DNA synthesizer (e.g., DNA Synthesizer Model 8905, PerSeptive Biosystems).

2. Preparation of the Protein of the Present Invention

The protein of the present invention can be produced by expressing the DNA of the present invention obtained by the method described in 1 above in host cells according to the methods described in Molecular Cloning, Second Edition, Current Protocols in Molecular Biology, etc., e.g., in the following manner.

On the basis of the DNA of the present invention, a DNA fragment of an appropriate length comprising a region encoding the protein is prepared according to need. The yield of the protein can be improved by replacing a nucleotide in the nucleotide sequence of the protein-encoding region so as to make a codon most suitable for the expression in a host cell.

The prepared DNA fragment is inserted downstream of a promoter region in an appropriate expression vector to construct a recombinant vector.

Then, the recombinant vector is introduced into a host cell suited for the expression vector, whereby a transformant which produces the protein of the present invention can be obtained.

As the host cell, any bacterial cells, yeast cells, animal cells, insect cells, plant cells, etc. which are capable of expressing the desired gene can be used.

The expression vectors that can be employed are those capable of autonomous replication or integration into chromosome in the above host cells and comprising a promoter at a position appropriate for the transcription of the DNA of the present invention.

When a procaryotic cell such as a bacterial cell is used as the host cell, it is preferred that the expression vector for the gene encoding the protein of the present invention is a recombinant DNA which is capable of autonomous replication in the procaryotic cell and which comprises a promoter, a ribosome binding sequence, the DNA of the present invention, and a transcription termination sequence. The vector may further comprise a gene regulating the promoter.

Examples of suitable expression vectors are pBTrp2, pBTac1 and pBTac2 (all available from Boehringer Mannheim), pKK233-2 (Pharmacia), pGEX (Pharmacia), pSE280 (Invitrogen), pGEMEX-1 (Promega), pQE-8 (QIAGEN), pET-3 (Novagen), pKYP10 (Japanese Published Unexamined Patent Application No. 110600/83), pKYP200 [Agric. Biol. Chem., 48, 669 (1984)], pLSA1 [Agric. Biol. Chem., 53, 277 (1989)], pGEL1 [Proc. Natl. Acad. Sci. USA, 82, 4306 (1985)], pBluescript II SK+ (Stratagene), pBluescript II SK(-) (Stratagene), pTrS30 [prepared from *Escherichia coli* JM109/pTrS30 (FERM BP-5407)], pTrS32 [prepared from *Escherichia coli* JM109/pTrS32 (FERM BP-5408)], pUC19 [Gene, 33, 103 (1985)], pSTV28 (Takara Shuzo Co., Ltd.), pUC118 (Takara Shuzo Co., Ltd.) and pPA1 (Japanese Published Unexamined Patent Application No. 233798/88).

As the promoter, any promoters capable of functioning in host cells such as *Escherichia coli* can be used. For example, promoters derived from *Escherichia coli* or phage, such as trp promoter (Ptrp), lac promoter (Plac), $P_L$ promoter, $P_R$ promoter and $P_{SE}$ promoter, SPO1 promoter, SPO2 promoter and penP promoter can be used. Artificially modified promoters such as a promoter in which two Ptrp are combined in tandem (Ptrp×2), tac promoter, lacT7 promoter and letI promoter, etc. can also be used.

It is preferred to use a plasmid in which the distance between the Shine-Dalgarno sequence (ribosome binding sequence) and the initiation codon is adjusted to an appropriate length (e.g., 6–18 bases).

In the recombinant DNA of the present invention, the transcription termination sequence is not essential for the expression of the DNA of the present invention, but it is preferred that the transcription termination sequence lie immediately downstream of the structural gene.

Examples of suitable procaryotes are microorganisms belonging to the genera *Escherichia, Serratia, Bacillus, Brevibacterium, Corynebacterium, Microbacterium* and *Pseudomonas*, specifically, *Escherichia coli* XL1 -BLlue, *Escherichia coli* XL2-Blue, *Escherichia coli* DH1, *Escherichia coli* MC1000, *Escherichia coli* KY3276, *Escherichia coli* W1485, *Eschericha coli* JM109, *Escherichia coli* HB101, *Escherichia coli* No. 29, *Escherichia coli* W3110, *Escherichia coli* NY49, *Serratia ficaria, Serratia fonticola, Serratia liquefaciens, Serratia marcescens, Bacillus subtilis, Bacillus amyloliquefaciens, Brevibacterium ammoniagenes, Brevibacterium immariophilium* ATCC 14066, *Corynebacterium glutamicum* ATCC 13032, *Corynebacterium glutamicum* ATCC 14067, *Corynebacterium glutamicum* ATCC 13869, *Corynebacterium acetoacidophilum* ATCC 13870, *Microbacterium ammoniaphilum* ATCC 15354 and *Pseudomonas* sp. D-0110.

Introduction of the recombinant DNA can be carried out by any of the methods for introducing DNA into the above host cells, for example, the method using calcium ion [Proc. Natl. Acad. Sci. USA, 69, 2110 (1972)], the photoplast method (Japanese Published Unexamined Patent Application No. 248394/88) and electroporation [Nucleic Acids Research, 16, 6127 (1988)].

When a yeast cell is used as the host cell, YEp13 (ATCC 37115), YEp24 (ATCC 37051), YCp50(ATCC 37419), pHS19, pHS15, etc. can be used as the expression vector.

As the promoter, any promoters capable of functioning in yeast cells can be used. Suitable promoters include PHO5 promoter, PGK promoter, GAP promoter, ADH promoter, gal 1 promoter, gal 10 promoter, heat shock polypeptide promoter, MFα 1 promoter, CUP 1 promoter, etc.

Examples of suitable host cells are cells of yeast strains belonging to the genera Saccharomyces, Schizosaccharomyces, Kluyveromyces, Trichosporon, Schwanniomyces and Pichia, specifically, *Saccharomyces cerevisiae, Schizosaccharomyces pombe, Kluyveromyces lactis, Trichosporon pullulans, Schwanniomyces alluvius* and *Pichia pastoris*.

Introduction of the recombinant DNA can be carried out by any of the methods for introducing DNA into yeast cells, for example, electroporation [Methods in Enzymol., 194, 182 (1990)], the spheroplast method [Proc. Natl. Acad. Sci. USA, 81, 4889 (1984)], the lithium acetate method [J. Bacteriol., 153, 163 (1983)] and the method described in Proc. Natl. Acad. Sci. USA, 75, 1929 (1978).

When an animal cell is used as the host cell, pcDNAI, pcDM8 (commercially available from Funakoshi), pAGE107 (Japanese Published Unexamined Patent Application No. 22979/91), pAS3-3 (Japanese Published Unexamined Patent Application No. 227075/90), pCDM8 [Nature, 329, 840 (1987)], pcDNAI/Amp (Invitrogen), pREP4 (Invitrogen), pAGE103 [J. Biochem., 101, 1307 (1987)], pAGE210, pAMo, pAMoA, etc. can be used as the expression vector.

As the promoter, any promoters capable of functioning in animal cells can be used. Suitable promoters include the promoter of IE (immediate early) gene of cytomegalovirus (CMV), SV40 early promoter, metallothionein promoter, the promoter of a retrovirus, heat shock promoter, SR α promoter, etc. The enhancer of IE gene of human CMV may be used in combination with the promoter.

Examples of suitable host cells are mouse myeloma cells, rat myeloma cells, mouse hybridomas, human-derived Namalwa cells and Namalwa KJM-1 cells, human embryonic kidney cells, human leukemia cells, African green monkey kidney cells, Chinese hamster-derived CHO cells and HBT5637 (Japanese Published Unexamined Patent Application No. 299/88).

The mouse myeloma cells include SP2/0, NSO, etc.; the rat myeloma cless include YB2/0, etc.; the human embryonic kidney cells include HEK293 (ATCC: CRL-1573), etc.; the human leukemia cells include BALL-1 etc.; and the African green monkey kidney cells include COS-1, COS-7, etc.

Introduction of the recombinant DNA can be carried out by any of the methods for introducing DNA into animal cells, for example, electroporation [Cytotechnology, 3, 133 (1990)], the calcium phosphate method (Japanese Published Unexamined Patent Application No. 227075/90), lipofection [Proc. Natl. Acad. Sci. USA, 84, 7413 (1987)], and the method described in Virology, 52, 456 (1973).

When an insect cell is used as the host cell, the protein can be expressed by using the methods described in Baculovirus Expression Vectors, A Laboratory Manual, W. H. Freeman and Company, New York (1992), Current Protocols in Molecular Biology, Molecular Biology, A Laboratory Manual, Bio/Technology, 6, 47 (1988), etc.

That is, the recombinant gene transfer vector and a baculovirus are cotransfected into an insect cell to obtain a recombinant virus in the culture supernatant of the insect cell, and then an insect cell is infected with the recombinant virus, whereby the protein can be expressed.

Examples of the gene transfer vectors suitable for use in this method are pVL1392, pVL1393 and pBlueBacIII (products of Invitrogen).

An example of the baculovirus is *Autographa californica* nuclear polyhedrosis virus, which is a virus infecting insects belonging to the family Barathra.

Examples of the insect cells are ovarian cells of *Spodoptera frugiperda*, ovarian cells of *Trichoplusia ni*, and silkworm ovary-derived cell lines.

The ovarian cells of *Spodoptera frugiperda* include Sf9, Sf21 (Baculovirus Expression Vectors, A Laboratory Manual), etc; the ovarian cells of *Trichoplusia ni* include High 5, BTI-TN-5B1-4 (Invitrogen), etc; and the silkworm ovary-derived cell lines include *Bombyx mori* N4, etc.

Cotransfection of the above recombinant gene transfer vector and the above baculovirus into an insect cell for the preparation of the recombinant virus can be carried out by the calcium phosphate method (Japanese Published Unexamined Patent Application No. 227075/90), lipofection [Proc. Natl. Acad. Sci. USA, 84, 7413 (1987)], etc.

When a plant cell is used as the host cell, Ti plasmid, tobacco mosaic virus vector, etc. can be used as the expression vector.

As the promoter, any promoters capable of functioning in plant cells can be used. Suitable promoters include 35S promoter of cauliflower mosaic virus (CaMV), rice actin 1 promoter, etc.

Examples of suitable host cells are cells of plants such as tobacco, potato, tomato, carrot, soybean, rape, alfalfa, rice, wheat and barley.

Introduction of the recombinant vector can be carried out by any of the methods for introducing DNA into plant cells, for example, the Agrobacterium method (Japanese Published Unexamined Patent Applications Nos. 140885/84 and 70080/85, WO 94/00977), electroporation (Japanese Published Unexamined Patent Application No. 251887/85) and the method using particle gun (gene gun) (Japanese Patents Nos. 2606856 and 2517813).

Expression of the gene can be carried out not only by direct expression but also by expression as a secretory protein, a fused protein, etc. according to the methods described in Molecular Cloning, Second Edition, etc.

When the gene is expressed in a yeast cell, an animal cell, an insect cell or a plant cell, a glycosylated protein can be obtained.

The protein of the present invention can be produced by culturing the transformant obtained as above in a medium, allowing the protein of the present invention to form and accumulate in the culture, and recovering the protein from the culture.

Culturing of the transformant of the present invention can be carried out by conventional methods for culturing the host cell of the transformant.

For the culturing of the transformant prepared by using a procaryotic cell such as *Escherichia coli* cell or a eucaryotic cell such as a yeast cell as the host cell, any of natural media and synthetic media can be used insofar as it is a medium suitable for efficient culturing of the transformant which contains carbon sources, nitrogen sources, inorganic salts, etc. which can be assimilated by the host used.

As the carbon sources, any carbon sources which can be assimilated by the host can be used. Examples of suitable carbon sources include carbohydrates such as glucose, fructose, sucrose, molasses containing them, starch and starch hydrolyzate; organic acids such as acetic acid and propionic acid; and alcohols such as ethanol and propanol.

As the nitrogen sources, ammonia, ammonium salts of inorganic or organic acids such as ammonium chloride, ammonium sulfate, ammonium acetate and ammonium phosphate, and other nitrogen-containing compounds can be used as well as peptone, meat extract, yeast extract, corn steep liquor, casein hydrolyzate, soybean cake, soybean cake hydrolyzate, and various fermented cells and digested products thereof.

Examples of the inorganic substances include potassium dihydrogenphosphate, dipotassium hydrogenphosphate, magnesium phosphate, magnesium sulfate, sodium chloride, ferrous sulfate, manganese sulfate, copper sulfate and calcium carbonate.

Culturing is usually carried out under aerobic conditions, for example, by shaking culture or submerged spinner culture under aeration, at 15–40° C. for 5 hours to 7 days. The pH is maintained at 3.0–9.0 during the culturing. The pH adjustment is carried out by using an organic or inorganic acid, an alkali solution, urea, calcium carbonate, ammonia, etc.

If necessary, antibiotics such as ampicillin and tetracycline may be added to the medium during the culturing.

When a microorganism transformed with an expression vector comprising an inducible promoter is cultured, an inducer may be added to the medium, if necessary. For example, in the case of a microorganism transformed with an expression vector comprising lac promoter, isopropyl-β-D-thiogalactopyranoside or the like may be added to the medium; and in the case of a microorganism transformed with an expression vector comprising trp promoter, indoleacrylic acid or the like may be added.

For the culturing of the transformant prepared by using an animal cell as the host cell, generally used media such as RPMI1640 medium [The Journal of the American Medical Association, 199, 519 (1967)], Eagle's MEM [Science, 122, 501 (1952)], DMEM [Virology, 8, 396 (1959)] and 199 medium [Proceeding of the Society for the Biological Medicine, 73, 1 (1950)], media prepared by adding fetal calf serum or the like to these media, etc. can be used as the medium.

Culturing is usually carried out at pH 6–8 at 25–40° C. for 1–7 days in the presence of 5% $CO_2$.

If necessary, antibiotics such as kanamycin, penicillin and streptomycin may be added to the medium during the culturing.

For the culturing of the transformant prepared by using an insect cell as the host cell, generally used media such as TNM-FH medium (Pharmingen), Sf-900II SFM medium (Life Technologies), ExCell 400 and ExCell 405 (JRH Biosciences) and Grace's Insect Medium [Nature, 195, 788 (1962)] can be used as the medium.

Culturing is usually carried out at pH 6–7 at 25–30° C. for 1–5 days.

If necessary, antibiotics such as gentamicin may be added to the medium during the culturing.

The transformant prepared by using a plant cell as the host cell may be cultured in the form of cells as such or after differentiation into plant cells or plant organs. For the culturing of such transformant, generally used media such as Murashige-Skoog (MS) medium and White medium, media prepared by adding phytohormones such as auxin and cytokinin to these media, etc. can be used as the medium.

Culturing is usually carried out at pH 5–9 at 20–40° C. for 3–60 days.

If necessary, antibiotics such as kanamycin and hygromycin may be added to the medium during the culturing.

As described above, the protein of the present invention can be produced by culturing a transformant prepared by introducing a recombinant vector comprising DNA encoding the protein of the present invention into a microorganism, animal cell or plant cell according to a conventional culturing method, allowing the protein to form and accumulate in the culture, and recovering the protein from the culture.

The protein of the present invention may be produced intracellularly, secreted extracellularly or produced on outer membranes by host cells. Such production methods can be selected according to the kind of host cell used or the structure of protein to be produced.

When the protein of the present invention is produced in host cells or on outer membranes of host cells, it is possible to force the protein to be secreted outside the host cells by applying the method of Paulson, et al. [J. Biol. Chem., 264, 17619 (1989)], the method of Lowe, et al. [Proc. Natl. Acad. Sci. USA, 86, 8227 (1989); Genes Develop., 4, 1288 (1990)], or the methods described in Japanese Published Unexamined Patent Applications Nos. 336963/93 and 823021/94, etc.

That is, extracellular secretion of the protein of the present invention can be caused by expressing it in the form of a protein in which a signal peptide is added upstream of a protein containing the active site of the protein of the present invention by the use of recombinant DNA techniques.

It is also possible to increase the protein production by utilizing a gene amplification system using a dihydrofolate reductase gene or the like according to the method described in Japanese Published Unexamined Patent Application No. 227075/90.

Further, it is possible to cause animal or plant cells carrying the introduced gene to redifferentiate in order to produce an animal (transgenic non-human animal) or plant (transgenic plant) having the introduced gene and to produce the protein of the present invention by using such an animal or plant.

When the transformant is an animal or plant, the protein can be produced by raising or culturing the animal or plant in a usual manner, allowing the protein to form and accumulate therein, and recovering the protein from the animal or plant.

The protein of the present invention can be produced using an animal, for example, by introducing the gene into an animal according to known methods [American Journal of Clinical Nutrition, 63, 639S (1996); American Journal of Clinical Nutrition, 63, 627S (1996); Bio/Technology, 9, 830 (1991)] and producing the protein in the animal carrying the gene.

The process for producing the protein of the present invention using an animal comprises, for example, raising a transgenic non-human animal in which the DNA encoding the protein of the present invention has been introduced, allowing the protein to form and accumulate in the animal, and recovering the protein from the animal. The places where the protein is formed and accumulated include milk (Japanese Published Unexamined Patent Application No. 309192/88), egg, etc. of the animal. As the promoter, any promoters capable of functioning in an animal can be used. Preferred promoters include mammary gland cell-specific promoters such as α casein promoter, β casein promoter, β lactoglobulin promoter and whey acidic protein promoter.

The process for producing the protein of the present invention using a plant comprises, for example, culturing a transgenic plant in which the DNA encoding the protein of the present invention has been introduced according to known culturing methods [Soshiki Baiyo (Tissue Culture), 20 (1994); Soshiki Baiyo (Tissue Culture), 21 (1995); Trends in Biotechnology, 15, 45 (1997)], allowing the protein to form and accumulate in the plant, and recovering the protein from the plant.

The protein produced by the transformant of the present invention can be isolated and purified by conventional methods for isolating and purifying enzymes.

For example, when the protein of the present invention is expressed in a soluble form in cells, the isolation and purification can be carried out in the following manner. After the completion of culturing, the cells are recovered from the culture by centrifugation and suspended in an aqueous buffer, followed by disruption using an ultrasonic disrupter, a French press, a Manton Gaulin homogenizer, a Dyno Mill, etc. to obtain a cell-free extract.

The cell-free extract is centrifuged to obtain the supernatant, and a purified protein preparation can be obtained from this supernatant by using ordinary means for isolation and purification of enzymes, for example, extraction with a solvent, salting-out with ammonium sulfate, etc., desalting, precipitation with an organic solvent, anion exchange chromatography using resins such as diethylaminoethyl (DEAE)-Sepharose and DIAION HPA-75 (Mitsubishi Kasei Corporation), cation exchange chromatography using resins such as S-Sepharose FF (Pharmacia), hydrophobic chromatography using resins such as butyl Sepharose and phenyl Sepharose, gel filtration using a molecular sieve, affinity chromatography, chromatofocusing, and electrophoresis such as isoelectric focusing, alone or in combination.

When the protein is expressed as an inclusion body in cells, the cells are similarly recovered and disrupted, followed by centrifugation to obtain a precipitate fraction. After the protein is recovered from the precipitate fraction by an ordinary method, the inclusion body of the protein is solubilized with a protein-denaturing agent.

The solubilized protein solution is diluted with or dialyzed against a solution containing no protein-denaturing agent or containing the protein-denaturing agent at such a low concentration that denaturation of protein is not caused to restore the normal protein structure, followed by the same isolation and purification steps as mentioned above to obtain a purified protein preparation.

When the protein of the present invention or its derivative such as glycosylated form is extracellularly secreted, the protein or its derivative such as glycosylated form can be recovered from the culture supernatant.

That is, the culture is treated by the above-described means such as centrifugation, and the obtained soluble fraction is subjected to the same isolation and purification steps as mentioned above to obtain a purified protein preparation.

An example of the protein obtained by the above method is the protein having the amino acid sequence shown in SEQ ID NO: 1.

It is also possible to produce the polypeptide of the present invention as a fusion protein with another protein and to purify it by affinity chromatography using a substance having affinity for the fused protein. For example, according to the method of Lowe, et al. [Proc. Natl. Acad. Sci. USA, 86, 8227 (1989); Genes Develop., 4, 1288 (1990)] and the methods described in Japanese Published Unexamined Patent Applications Nos. 336963/93 and 823021/94, the polypeptide of the present invention can be produced as a fusion protein with protein A and can be purified by affinity chromatography using immunoglobulin G.

Further, it is possible to produce the polypeptide of the present invention as a fusion protein with a Flag peptide and to purify it by affinity chromatography using anti-Flag antibody [Proc. Natl. Acad. Sci. USA, 86, 8227 (1989); Genes Develop., 4, 1288 (1990)]. The polypeptide can also be purified by affinity chromatography using an antibody against said polypeptide itself.

On the basis of the amino acid information of the protein obtained as above, the protein of the present invention can be produced by chemical synthetic methods such as the Fmoc method (the fluorenylmethyloxycarbonyl method) and the tBoc method (the t-butyloxycarbonyl method). Further, the protein can be chemically synthesized by using peptide synthesizers (Advanced ChemTech, Perkin-Elmer, Pharmacia, Protein Technology Instrument, Synthecell-Vega, PerSeptive, Shimadzu Corporation, etc.).

3. Preparation of a Galactose-containing Carbohydrate

A galactose-containing carbohydrate can be produced in an aqueous medium using the culture of the transformant obtained by the culturing described in 2 above or treated matters thereof obtained by treating the culture by various means as an enzyme source.

The treated matters of the culture include concentrated culture, dried culture, cells obtained by centrifuging the culture, products obtained by treating the cells by various means such as drying, freeze-drying, freezing treatment with a surfactant, unitrasonication, mechanical friction, treatment with a solvent, enzymatic treatment, protein fractionation and immobilization, an enzyme preparation obtained by extracting the cells, etc. When frozen cells are used as the enzyme source, they are thawed before each use.

The enzyme source to be used for the preparation of the galactose-containing carbohydrate is used at a concentration of 0.1 mU/l–10000 U/l, preferably 1 mU/l–1000 U/l, one unit (U) being defined as the activity which forms 1 μmole of the galactose-containing carbohydrate at 37° C. in one minute.

Aqueous media useful in the preparation of the galactose-containing carbohydrate include water, buffers such as phosphate buffer, carbonate buffer, acetate buffer, borate buffer, citrate buffer and Tris buffer, alcohols such as methanol and ethanol, esters such as ethyl acetate, ketones such as acetone, amides such as acetamide, etc. Also useful is the culture of the microorganism used as an enzyme source.

If necessary, a surfactant or an organic solvent may be added in the process for preparing the galactose-containing carbohydrate. Any surfactant that promotes the formation of the galactose-containing carbohydrate can be used. Suitable surfactants include nonionic surfactants such as polyoxyethylene octadecylamine (e.g., Nymeen S-215, NOF Corporation), cationic surfactants such as cetyltrimethylammonium bromide and alkyldimethyl benzylammonium chloride (e.g., Cation F2–40E, NOF Corporation), anionic surfactants such as lauroyl sarcosinate, and tertiary amines such as alkyldimethylamine (e.g., Tertiary Amine FB, NOF Corporation), which may be used alone or in combination. The surfactant is usually used at a concentration of 0.1–50 g/l. As the organic solvent, xylene, toluene, aliphatic alcohols, acetone, ethyl acetate, etc. may be used usually at a concentration of 0.1–50 ml/l.

The sugar nucleotide substrate to be used in the preparation of the galactose-containing carbohydrate, uridine diphosphogalactose (UDP-Gal), may be a commercially available one, a reaction mixture obtained by utilizing the activity of a microorganism or the like, or a purified product obtained from such reaction mixture.

The sugar nucleotide substrate is used at a concentration of 0.1–500 mM.

Any acceptor carbohydrate that can be a substrate for glycosyltransferase may be used as the acceptor carbohydrate for the preparation of the galactose-containing carbohydrate. Suitable acceptor carbohydrates include glucose (Glc), N-acetylglucosamine (GlcNAc), GlcNAc β1–3Gal β1–4Glc (LNT-2), oligosaccharides having Glc or GlcNAc at the non-reducing terminus, etc.

The acceptor carbohydrate is used at a concentration of 0.1–500 mM.

If necessary, an inorganic salt (e.g., $MnCl_2$), β-mercaptoethanol, etc. may be added in the reaction for forming the galactose-containing carbohydrate.

The reaction for forming the galactose-containing carbohydrate is carried out in an aqueous medium at pH 5–10, preferably pH 6–8, at 20–50° C. for 1–96 hours.

The galactose-containing carbohydrate formed in the aqueous medium can be determined according to a known method [Kagaku to Kogyo (Chemistry and Industry), 43, 953 (1990)].

The galactose-containing carbohydrate can be recovered from the reaction mixture by ordinary methods using active carbon, ion-exchange resins, etc.; for instance, N-acetyllactosamine can be recovered according to the method described in J. Org. Chem., 47, 5416 (1982).

BRIEF DESCRIPTION OF THE DRAWINGS

FIG. 1.

FIG. 2.

FIG. 3.

Figure 1:
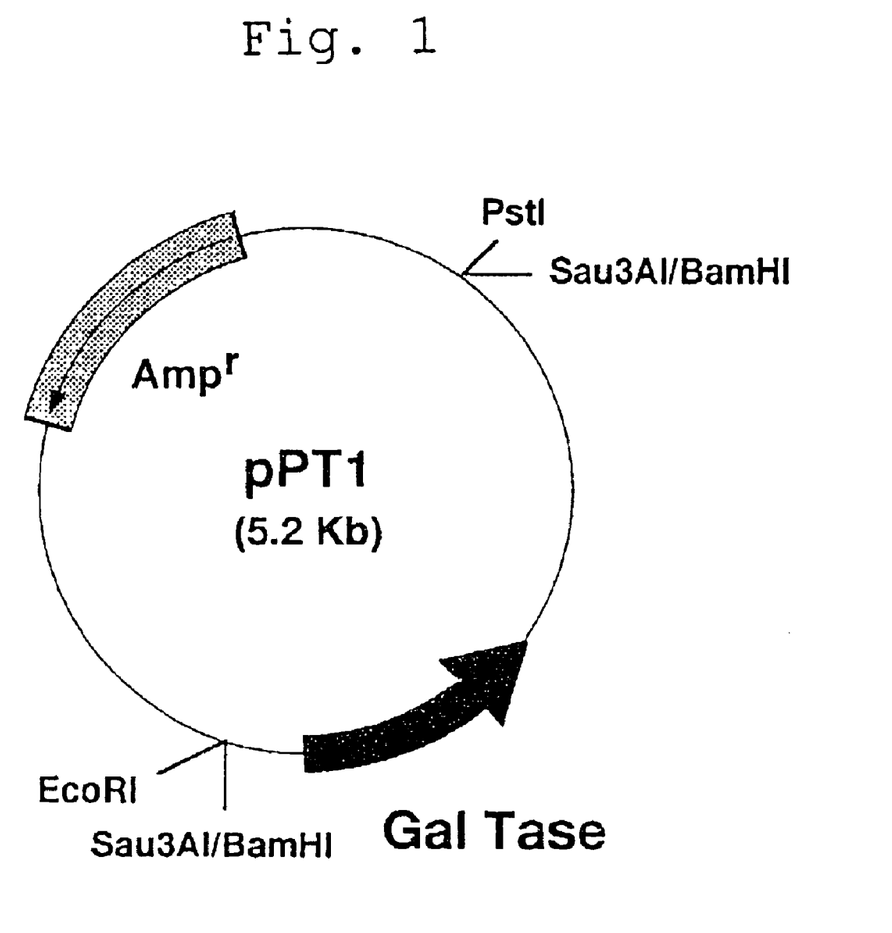
FIG. 1 shows the structure of plasmid pPT1 expressing β1,4-galactosyltransferase gene.
Figure 2:
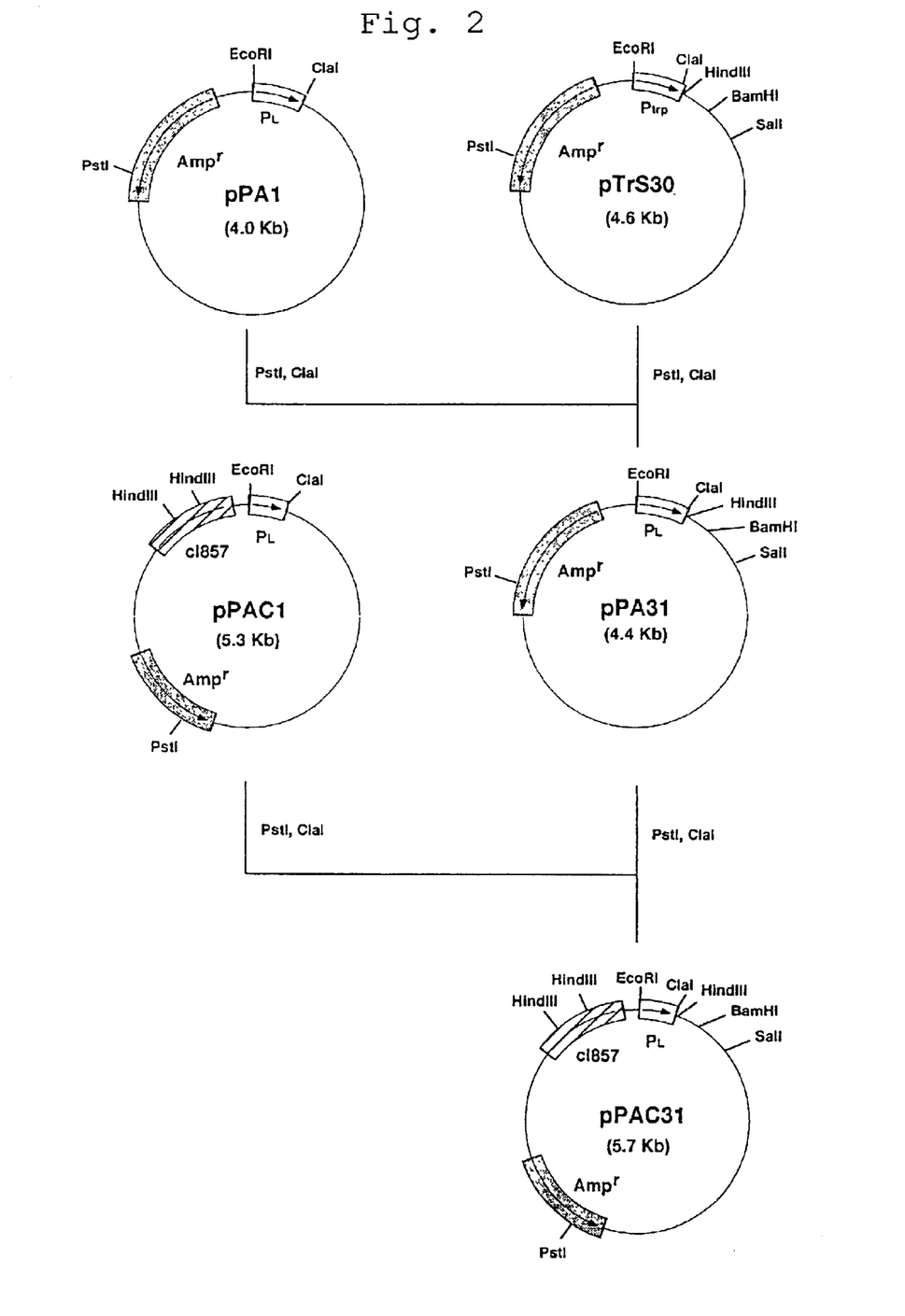
FIG. 2 shows the steps for constructing expression plasmids pPA31 and pPAC31.
Figure 3:
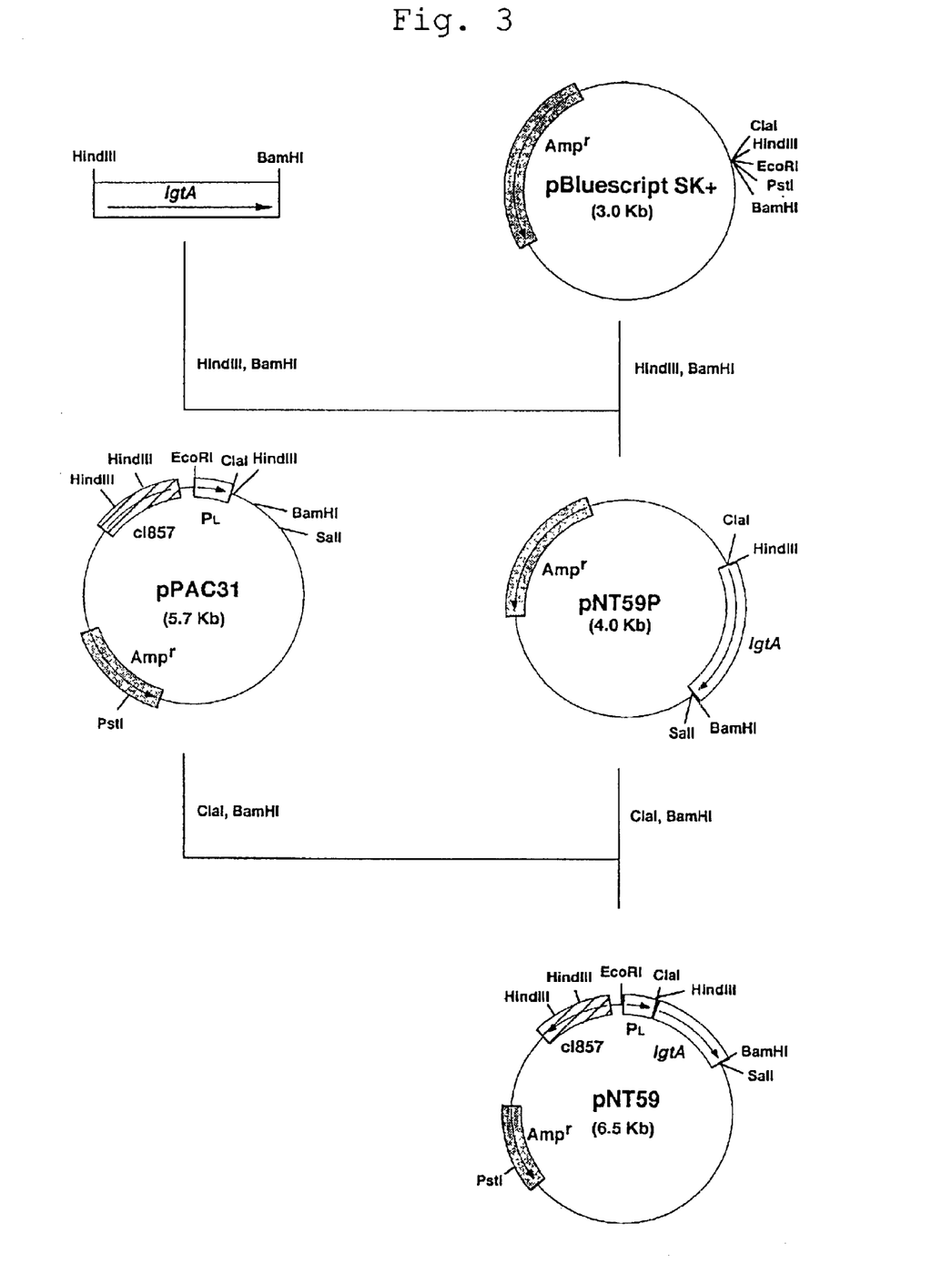
FIG. 3 shows the steps for constructing plasmid pNT59 expressing lgtA gene.

EXPLANATION OF SYMBOLS $Amp^r$: Ampicillin resistance gene
$P_{trp}$: Tryptophan promoter
$P_L$: $P_L$ promoter
cI857: cI857 repressor
lgtA: β1,3-N-acetylglucosaminyltransferase gene
Gal Tase: β1,4-galactosyltransferase gene Certain embodiments of the present invention are illustrated in the following examples. These examples are not to be construed as limiting the scope of the invention.

Examples of the present invention are shown below.

BEST MODES FOR CARRYING OUT THE INVENTION

EXAMPLE 1

Construction of a *Helicobacter pylori* Genomic Library

*Helicobacter pylori* (NCTC 11637, ATCC 43504) was cultured by the method described in Mol. Microbiol., 20, 833 (1996).

After the culturing, the chromosomal DNA of the microorganism was isolated and purified by the method described in Current Protocols in Molecular Biology.

The chromosomal DNA (10 µg) was partially digested with restriction enzyme Sau3AI and fractionated by sucrose density gradient ultracentrifugation, and DNA fragmants of 2–6 kb were recovered.

The recovered DNA fragment (0.5 µg) and pUC118 DNA (0.2 µg, Takara Shuzo Co., Ltd.) which had been cleaved with restriction enzyme BamHI and treated with phosphatase were subjected to ligation reaction using a ligation kit (Takara Shuzo Co., Ltd.) at 16° C. for 16 hours.

*Escherichia coli* NM522 was transformed using the ligation mixture according to the known method described above, spread on LB agar medium [10 g/l Bacto-tryptone (Difco Laboratories Inc.), 5 g/l yeast extract (Difco Laboratories Inc.), 5 g/l NaCl (pH 7.2) and 15 g/l agar] containing 50 µg/ml ampicillin, and cultured overnight at 30° C.

The transformants that grew on the medium were subjected to screening for a β1,4-galactosyltransferase gene.

EXAMPLE 2

Screening

The *Escherichia coli* strains carrying the DNA fragment derived from *Helicobacter pylori* prepared in Example 1 were inoculated by groups of 10 into 0.8 ml of LB medium containing 50 µg/ml ampicillin in a 48-well micro plate, followed by culturing at 37° C. for 17 hours.

The resulting culture (150 µl) was centrifuged to obtain wet cells. The wet cells were stored at −20° C. and used after thawing.

The reaction for screening was carried out at 37° C. for 16 hours in 0.02 ml of a reaction mixture comprising the above wet cells of *Escherichia coli*, 50 mM MES (pH 6.0), 10 mM MnCl$_2$, 0.2 mM UDP-Gal, 0.4% Nymeen S-215 and 0.2 mM FCHASE-LNT-2 prepared in Reference Example 1 given below.

After the completion of reaction, the reaction mixture was centrifuged to remove the cells and to obtain the supernatant.

The supernatant was put on a silica gel-60 TLC plate (Merck & Co.), followed by development with ethyl acetate : methanol : water : acetic acid =7:2:1:0.1. After the development, the plate was dried and detection of spots was made with UV 365 nm.

The same procedure as above was repeated using 1,4-galactosyltransferase (Sigma Chemical Co.) in place of the *Escherichia coli* wet cells and the position of fluorescence-labeled lacto-N-neotetraose (FCHASE-LNnT) formed by this procedure on TLC was confirmed.

Strains were isolated from populations of *Escherichia coli* wet cells giving a spot at the same position on TLC as FCHASE-LNnT by single colony isolation. The isolated strains were subjected to similar screening, whereby a strain showing 1,4-galactosyltransferase activity (*Escherichia coli* NM522/pPT1) was selected.

*Escherichia coli* NM522/pPT1 was deposited with the National Institute of Bioscience and Human-Technology, Agency of Industrial Science and Technology, 1–3, Higashi 1-chome, Tsukuba-shi, Ibaraki-ken, 3050046 Japan, on Jan. 20, 1998 with accession number FERM BP-6226.

Structural analysis of plasmid pPT1 carried by this strain revealed that the plasmid had a structure wherein a 2 kb DNA fragment derived from *Helicobacter pylori* was inserted in plasmid pUC118 at the BamHI cleavage site, as shown in FIG. 1.

The nucleotide sequence of the 2 kb DNA insert was determined and was found to comprise the open reading frame (ORF) shown in SEQ ID NO: 2. The amino acid sequence corresponding to this ORF is shown in SEQ ID NO: 1.

EXAMPLE 3

Production of N-Acetyllactosamine

*Escherichia coli* NM522/pPT1 obtained in Example 2 was inoculated into 8 ml of LB medium containing 50 µg/ml ampicillin in a large test tube, and cultured at 28° C. for 17 hours. The resulting culture was inoculated into 8 ml of LB medium containing 50 µg/ml ampicillin in a large test tube in an amount of 1% and cultured at 37° C. for 5 hours. The resulting culture (0.1 ml) was centrifuged to obtain wet cells. The wet cells were stored at −20° C. and used after thawing.

Reaction was carried out at 37° C. for 16 hours in 0.1 ml of a reaction mixture comprising the above wet cells (obtained from 0.1 ml of the culture), 50 mM MES (pH 6.0), 10 mM MnCl$_2$, 0.2 mM GlcNAc, 0.2 mM UDP-Gal and 0.4% Nymeen S-215.

After the completion of reaction, the reaction product was analyzed by using a carbohydrate analysis system (DX-500, Dionex) and it was found that 12.7 mg/l N-acetyllactosamine was formed and accumulated in the reaction mixture.

EXAMPLE 4

Production of Lacto-N-neotetraose

*Escherichia coli* NM522/pPT1 obtained in Example 2 was inoculated into 8 ml of LB medium containing 50 µg/ml ampicillin in a large test tube, and cultured at 28° C. for 17 hours.

The resulting culture was inoculated into 8 ml of LB medium containing 50 µg/ml ampicillin in a large test tube in an amount of 1%, and cultured at 37° C. for 5 hours.

The resulting culture (0.1) ml) was centrifuged to obtain wet cells. The wet cells were stored at −20° C. and used after thawing.

Reaction was carried out at 37° C. for 16 hours in 0.1 ml of a reaction mixture comprising the above wet cells (obtained from 0.1 ml of the culture), 50 mM MES (pH 6.0), 10 mM MnCl$_2$, 0.2 mM UDP-Gal, 0.4% Nymeen S-215 and 0.2 mM LNT-2 prepared in Reference Example 2.

After the completion of reaction, the reaction product was analyzed by using a carbohydrate analysis system (DX-500, Dionex) and it was found that 61.6 mg/l lacto-N-neotetraose was formed and accumulated in the reaction mixture.

EXAMPLE 5

Construction of a Plasmid for High Expression of β1,4-galactosyltransferase Gene The sense DNA primer shown in SEQ ID NO: 3 and the antisense DNA primer shown in SEQ ID NO: 4 were synthesized by using a DNA synthesizer (Model 8905, PerSeptive Biosystems).

PCR was carried out using the above synthetic DNAs as primers and pPT1 plasmid DNA described in Example 2 as a template. That is, PCR was carried out by 30 cycles, one cycle consisting of reaction at 94° C. for one minute, reaction at 42° C. for 2 minutes and reaction at 72° C. for 3 minutes, using 40 µl of a reaction mixture comprising 1 ng of pPT1 DNA, 0.5 µM each of the primers, 2.5 units of Pfu DNA polymerase (Stratagene), 4 μl of buffer for Pfu DNA polymerase (10 ×) (Stratagene) and 200 μM each of deoxyNTPs.

One-tenth of the resulting reaction mixture was subjected to agarose gel electrophoresis to confirm that the desired fragment was amplified. Then, the remaining reaction mixture was mixed with an equal amount of phenol/chloroform (1 vol/1 vol) saturated with TE [10 mM Tris-HCl (pH 8.0), 1 mM EDTA], followed by centrifugation. The obtained upper layer was mixed with a two-fold volume of cold ethanol and allowed to stand at −80° C. for 30 minutes. The resulting mixture was centrifuged to obtain a DNA precipitate.

The DNA precipitate was dissolved in 20 μl of TE and 5 μl of the solution was subjected to reaction to cleave the DNA with restriction enzymes SacI and BamHI. DNA fragments were separated by agarose gel electrophoresis and a 0.9 kb fragment was recovered using Gene Clean II Kit. pPAC31 DNA described in Reference Example 1 (0.2 μg) was cleaved with restriction enzymes SacI and BamHI. DNA fragments were separated by agarose gel electrophoresis and a 5.5 kb fragment was recovered in the same manner.

The 0.9 kb fragment and 5.5 kb fragment obtained above were subjected to ligation reaction using a ligation kit at 16° C. for 16 hours. *Escherichia coli* NM522 was transformed using the ligation mixture according to the known method described above, spread on LB agar medium containing 50 μg/ml ampicillin, and cultured overnight at 30° C.

A plasmid was extracted from a colony of the transformant that grew on the medium according to the known method described above, whereby pPT7, which is a plasmid for high expression of β1,4-galactosyltransferase gene, was obtained.

EXAMPLE 6

Production of N-Acetyllactosamine

*Escherichia coli* NM522/pPT7 obtained in Example 5 and *Escherichia coli* NM522/pNT25/pNT32 (WO 98/12343) were respectively inoculated into 125 ml of LB medium containing 50 μg/ml ampicillin in a 1—1 Erlenmeyer flask with baffles, followed by culturing at 30° C. with stirring (220 r.p.m.) for 17 hours.

The resulting culture (125 ml) was inoculated into 2.5 l of a liquid medium (pH unadjusted) comprising 10 g/l glucose, 12 g/l Bacto-tryptone (Difco Laboratories Inc.), 24 g/l yeast extract (Difco Laboratories Inc.), 2.3 g/l $KH_2PO_4$ (separately sterilized), 12.5 g/l $K_2HPO_4$ (separately sterilized) and 50 μg/ml ampicillin in a 5-1 jar fermentor. Culturing was carried out at 30° C. for 4 hours and then at 40° C. for 3 hours, under the conditions of stirring at 600 r.p.m. and aeration at 2.5 l /min.

During the culturing, the pH of culture was maintained at 7.0 with 28% aqueous ammonia. Glucose (5 g/l–30 g/l) was added, according to need, in the course of culturing. The resulting culture was centrifuged to obtain wet cells. The wet cells were stored at −20° C. and used after thawing.

*Corynebacterium ammoniagenes* ATCC 21170 was inoculated into 20 ml of a liquid medium comprising 50 g/l glucose, 10 g/l polypeptone (Nihon Pharmaceutical Industrial Co., Ltd.), 10 g/l yeast extract (Oriental Yeast Co., Ltd.), 5 g/l urea, 5 g/l $(NH_4)_2SO_4$, 1 g/l $KH_2PO_4$, 3 g/l $K_2HPO_4$, 1 g/l $MgSO_4.7H_2O$, 0.1 g/l $CaCl_2.2H_2O$, 10 mg/l $FeSO_4.7H_2O$, 10 mg/l $ZnSO_4.7H_2O$, 20 mg/l $MnSO_4.4-6H_2O$, 20 mg/l L-cysteine, 10 mg/l calcium D-pantothenate, 5 mg/l vitamin B1,5 mg/l nicotinic acid and 30 μg/l biotin (adjusted to pH 7.2 with 10 N NaOH) in a 300-ml Erlenmeyer flask with baffles, followed by culturing at 28° C. with stirring (220 r.p.m.) for 24 hours.

The resulting culture (20 ml) was inoculated into 240 ml of a liquid medium having the same composition as above in a 2-1 Erlenmeyer flask with baffles, followed by culturing at 28° C. with stirring (220 r.p.m.) for 24 hours. The obtained culture was used as a seed culture.

The seed culture (250 ml) was inoculated into 2.5 l of a liquid medium comprising 150 g/l glucose, 5 g/l meat extract (Kyokuto Pharmaceutical Ind. Co., Ltd.), 10 g/l $KH_2PO_4$, 10 g/l $K_2HPO_4$, 10g/l $MgSO_4.7H_2O$, 0.1 g/l $CaCl_2.2H_2O$, 20mg/l $FeSO_4.7H_2O$, 10 mg/l $ZnSO_4.7H_2O$, 20 mg/l $MnSO_4.4-6H_2O$ (separately sterilized), 15 mg/l β-alanine (separately sterilized), 20 mg/l L-cysteine, 100 μg/l biotin, 2 g/l urea and 5 mg/l vitamin B1 (separately sterilized) (adjusted to pH 7.2 with 10 N NaOH) in a 5-1 jar fermentor. Culturing was carried out at 32° C. for 24 hours under the conditions of stirring at 600 r.p.m. and aeration at 2.5l/min. During the culturing, the pH of culture was maintained at 6.8 with 28% aqueous ammonia.

The resulting culture was centrifuged to obtain wet cells. The wet cells were stored at −20° C. and used after thawing.

A reaction mixture (30 ml) comprising 50 g/l *Escherichia coli* NM522/pPT7 wet cells, 40 g/l *Escherichia coli* NM522/pNT25/pNT32 wet cells, 150 g/l *Corynebacterium ammoniagenes* ATCC 21170 wet cells, 50 g/l galactose, 50 g/l fructose, 50 g/l GlcNAc, 15 g/l $KH_2PO_4$, 5 g/l $MgSO_4.7H_2O$, 5 g/l phytic acid, 10 g/l orotic acid (potassium salt), 4 g/l Nymeen S-215 and 10 ml/l xylene was put into a 200-ml beaker and subjected to reaction for 22 hours with stirring (900 r.p.m.) using a magnetic stirrer. During the reaction, the pH of reaction mixture was maintained at 7.2 with 4 N NaOH.

By this reaction, 60.0 g/l N-acetyllactosamine was formed in the reaction mixture.

REFERENCE EXAMPLE 1

Preparation of Fluorescence-Labeled LNT-2 (FCHASE-LNT-2

1. Preparation of Fluorescence-Labeled Lactose (FCHASE-Lac)

Fluorescence-labeled lactose (FCHASE-Lac) was prepared from aminophenyl lactose (Sigma Chemical Co.) And 6-(5-fluorescein-carboxamido)- hexanoic acid succinimidyl ester (FCHASE, Molecular Probes, Inc) according to a know method [J. Biol. Chem., 271, 19166 (1996)].

2. Construction of a Strain Expressing N-Acetylglucosaminyltransferase (1) Construction of Expression Vector pPAC31

Plasmid pTrS30 (FERM BP-5407) containing tryptophan promoter and plasmids pPA1 (Japanese Published Unexamined Patent Application No. 233798/88) and pPAC1 (FERM BP-6054) containing $P_L$ promoter were respectively isolated and purified from the strains carrying these plasmids according to known methods.

pTrS30 DNA (0.2 μg) was cleaved with restriction enzymes PstI and ClaI. DNA fragments were separated by agarose gel electrophoresis and a 3.4 kb fragment was recovered using Gene Clean II Kit (Bio 101). pPA1 DNA (0.5 μg) was cleaved with restriction enzymes PstI and ClaI. DNA fragments were separated by agarose gel electrophoresis and a 1.0 kb fragment was recovered in the same manner.

The 3.4 kb fragment and 1.0 kb fragment obtained above were subjected to ligation reaction using a ligation kit at 16° C. for 16 hours. *Escherichia coli* NM522 was transformed using the ligation mixture according to the known method described above, spread on LB agar medium containing 50 μg/ml ampicillin, and cultured overnight at 37° C.

A plasmid was extracted from a colony of the transformant that grew on the medium according to the known method described above, whereby pPA31, which is an expression vector containing $P_L$ promoter, was obtained. The structure of this plasmid was confirmed by digestion with restriction enzymes (FIG. 2).

pPA31 DNA (0.2/ μg) was cleaved with restriction enzymes PstI and ClaI. DNA fragments were separated by agarose gel electrophoresis and a 3.4 kb fragment was recovered using Gene Clean II Kit. pPAC1 DNA (0.5/μg) was cleaved with restriction enzymes PstI and ClaI. DNA fragments were separated by agarose gel electrophoresis and a 2.3 kb fragment was recovered in the same manner.

The 3.4 kb fragment and 2.3 kb fragment obtained above were subjected to ligation reaction using a ligation kit at 16° C. for 16 hours. *Escherichia coli* NM522 was transformed using the ligation mixture according to the known method described above, spread on LB agar medium containing 50 μg/ml ampicillin, and cultured overnight at 37° C.

A plasmid was extracted from a colony of the transformant that grew on the medium according to the known method described above, whereby pPAC31, which is an expression vector containing $P_L$ promoter and cI857 repressor, was obtained.

The structure of this plasmid was confirmed by digestion with restriction enzymes (FIG. 2).

(2) Construction of lgtA Expression Plasmid

The chromosomal DNA of *Neisseria gonorrhoeae* ATCC 33084 was isolated and purified in the same manner as in Example 1.

The sense DNA primer shown in SEQ ID NO: 5 and the antisense DNA primer shown in SEQ ID NO: 6 were synthesized by using a DNA synthesizer (Model 8905, PerSeptive Biosystems).

PCR was carried out using the above synthetic DNAs as primers and the chromosomal DNA of *Neisseria gonorrhoeae* ATCC 33084 as a template. That is, PCR was carried out by 30 cycles, one cycle consisting of reaction at 94° C. for one minute, reaction at 42° C. for 2 minutes and reaction at 72° C. for 3 minutes, using 40 μl of a reaction mixture comprising 0.1 μg of the chromosomal DNA, 0.5 μM each of the primers, 2.5 units of Pfu DNA polymerase (Stratagene), 4 μl of buffer for Pfu DNA polymerase (10 ×) (Stratagene) and 200 μM each of deoxyNTPs.

One-tenth of the resulting reaction mixture was subjected to agarose gel electrophoresis to confirm that the desired fragment was amplified. Then, the remaining reaction mixture was mixed with an equal amount of phenol/chloroform (1 vol/1 vol) saturated with TE [10 mM Tris-HCl (pH 8.0), 1 mM EDTA], followed by centrifugation. The obtained upper layer was mixed with a two-fold volume of cold ethanol and allowed to stand at −80° C. for 30 minutes. The resulting mixture was centrifuged to obtain a DNA precipitate.

The DNA precipitate was dissolved in 20 μl of TE and 5 μl of the solution was subjected to reaction to cleave the DNA with restriction enzymes HindIII and BamHI. DNA fragments were separated by agarose gel electrophoresis and a 1.0 kb fragment was recovered using Gene Clean II Kit. pBluescript II SK+DNA (0.2 μg) was cleaved with restriction enzymes HindIII and BamHI. DNA fragments were separated by agarose gel electrophoresis and a 3.0 kb fragment was recovered in the same manner.

The 1.0 kb fragment and 3.0 kb fragment obtained above were subjected to ligation reaction using a ligation kit at 16° C. for 16 hours. *Escherichia coli* NM522 was transformed using the ligation mixture according to the known method described above, spread on LB agar medium containing 50 μg/ml ampicillin, and cultured overnight at 30° C.

A plasmid was extracted from a colony of the transformant that grew on the medium according to the known method described above, whereby pNT59P, which is an lgtA expression plasmid, was obtained. The structure of this plasmid was confirmed by digestion with restriction enzymes (FIG. 3).

pNT59P DNA (0.5 μg) was cleaved with restriction enzymes ClaI and BamHI. DNA fragments were separated by agarose gel electrophoresis and a 1.0 kb fragment was recovered using Gene Clean II Kit. pPAC31 DNA constructed above (0.2 μg) was cleaved with restriction enzymes ClaI and BamHI. DNA fragments were separated by agarose gel electrophoresis and a 5.5 kb fragment was recovered in the same manner.

The 1.0 kb fragment and 5.5 kb fragment obtained above were subjected to ligation reaction using a ligation kit at 16° C. for 16 hours. Escherichia coli NM522 was transformed using the ligation mixture according to the known method described above, spread on LB agar medium containing 50 α g/ml ampicillin, and cultured overnight at 30° C.

A plasmid was extracted from a colony of the transformant that grew on the medium according to the known method described above, whereby pNT59, which is an lgtA expression plasmid, was obtained. The structure of this plasmid was confirmed by digestion with restriction enzymes (FIG. 3).

3. Preparation of Fluorescence-Labeled LNT-2 (FCHASE-LNT-2)

*Escherichia coli* NM522/pNT59 obtained above was inoculated into 8 ml of LB medium containing 50 α g/ml ampicillin in a large test tube, and cultured at 28° C. for 17 hours. The resulting culture was inoculated into 8 ml of LB medium containing 50 α g/ml ampicillin in a large test tube in an amount of 1%, and cultured at 28° C. for 4 hours and then at 40° C. for 3 hours.

The resulting culture was centrifuged to obtain wet cells. The wet cells were stored at −20° C. and used after thawing.

Reaction was carried out at 37° C. for 16 hours in 0.1 ml of a reaction mixture comprising 20 mg of the above wet cells, 50 mM MES (pH 6.0), 10 mM $MnCl_2$, 20 mM UDP-GlcNAc, 0.4% Nymeen S-215 and 20 mM FCHASE-Lac prepared in 1 above.

After the completion of reaction, the cells were removed from the reaction mixture by centrifugation and the obtained supernatant was subjected to TLC.

TLC was carried out by using a silica gel-60 TLC plate (Merck & Co.) and by using, as a developer, ethyl acetate methanol:water:acetic acid =7:2:1:0.1.

After the development, the TLC plate was dried and detection of spots was made with UV 365 nm.

The silica gel portion at the spot corresponding to FCHASE-LNT-2 on the TLC plate was scraped off and extracted with water, followed by centrifugation and filtration through a filter to remove the silica gel. The obtained product was freeze-dried, whereby FCHASE-LNT-2, which is a substrate, was obtained.

REFERENCE EXAMPLE 2

Preparation of LNT-2 Substrate

Lacto-N-neotetraose (Oxford Glycosystems) was acted on by β-galactosidase (Seikagaku Corporation) to completely remove galactose at its non-reducing terminus, followed by heat treatment at 100° C. for 5 minutes to inactivate the β-galactosidase. The resulting reaction mixture was used as LNT-2 substrate in the above example.

INDUSTRIAL APPLICABILITY

According to the present invention, β1,4-galactosyltransferase can be produced in large amounts by recombinant DNA techniques. Galactose-containing carbohydrates can be efficiently produced by the use of the enzyme.

What is claimed is:

1. A process for producing a galactose-containing carbohydrate, which comprises:

selecting an enzyme source comprising a culture of a transformed host cell harboring a DNA that has 95% or more homology to the nucleotide sequence shown in SEQ ID NO: 2 and encodes a protein having β 1,4-galactosyltransferase activity; and admixing said enzyme source with an acceptor carbohydrate and uridine diphosphogalactose in an aqueous medium.

2. The process according to claim 1, wherein said galactose-containing carbohydrate is lacto-N-neotetraose.

3. The process according to claim 1, wherein said protein comprises the peptide sequence of SEQ ID NO:1.

4. The process according to claim 3, wherein said galactose-containing carbohydrate is lacto-N-neotetraose.

5. The process according to claim 1, wherein said galactose-containing carbohydrate is N-acetyllactosamine.

6. The process according to claim 1, wherein said galactose-containing carbohydrate is N-acetyllactosamine.

* * * * *

UNITED STATES PATENT AND TRADEMARK OFFICE
CERTIFICATE OF CORRECTION

PATENT NO. : 6,830,908 B2
DATED : December 14, 2004
INVENTOR(S) : Satoshi Koizumi et al.

It is certified that error appears in the above-identified patent and that said Letters Patent is hereby corrected as shown below:

Title page,
Item [30], Foreign Application Priority Data, "Feb. 4, 1998 (JP).... 11-23389" should read -- Feb. 4, 1998 (JP) .... 10-23389 --.
Item [56], References Cited, OTHER PUBLICATIONS,
"Masri, et al.," reference "Bioch mical" should read -- Biochemical --.

Column 3,
Line 25, "(1984]," should read -- (1984)], --;
Line 29, "BP-5407," should read -- BP-5407), --; and
Line 33, ""(1990]," should read -- (1990)], --.

Column 4,
Line 22, "-3Galβ-1, 4Glc)" should read -- 3Galβ1, 4Glc) --.

Column 6,
Line 63, "cless" should read -- cells --.

Column 11,
Line 41, "unitrasonication," should read -- ultrasonication --.

Column 13,
Line 52, "1,4-" should read -- β1,4- --; and
Line 61, "1,4-galactosyltransferase" should read -- β1,4-galactosyltransferase --.

Column 14,
Line 41, "(0.1) ml)" should read -- (0.1 ml) --.

Column 18,
Lines 29 and 31, "50 α g/ml" should read -- 50 $\mu$ g/ml --; and
Line 44, "acetate" should read -- acetate: --.

UNITED STATES PATENT AND TRADEMARK OFFICE
CERTIFICATE OF CORRECTION

PATENT NO. : 6,830,908 B2
DATED : December 14, 2004
INVENTOR(S) : Satoshi Koizumi et al.

It is certified that error appears in the above-identified patent and that said Letters Patent is hereby corrected as shown below:

Column 24,
Line 3, "claim 1," should read -- claim 3, --.

Signed and Sealed this

Twenty-fourth Day of May, 2005

JON W. DUDAS
*Director of the United States Patent and Trademark Office*